United States Patent [19]

Kameishi

[11] Patent Number: 5,418,566
[45] Date of Patent: May 23, 1995

[54] COMPACT IMAGING APPARATUS FOR ELECTRONIC ENDOSCOPE WITH IMPROVED OPTICAL CHARACTERISTICS

[75] Inventor: Wataru Kameishi, Ootawara, Japan

[73] Assignee: Kabushiki Kaisha Toshiba, Kawasaki, Japan

[21] Appl. No.: 72,688

[22] Filed: Jun. 7, 1993

Related U.S. Application Data

[63] Continuation of Ser. No. 757,350, Sep. 10, 1991, abandoned.

[30] Foreign Application Priority Data

Sep. 10, 1990 [JP] Japan .................................. 2-237121

[51] Int. Cl.⁶ .......................................... H04N 5/335
[52] U.S. Cl. .................................... 348/294; 348/340; 348/65
[58] Field of Search .................. 358/55, 225, 229, 209, 358/213.11, 98; 357/80, 74, 79; 250/239, 578.1; 128/4, 6; H04N 5/335; 348/335, 336, 337, 344, 65, 207, 340, 374; 257/245, 246, 294

[56] References Cited

U.S. PATENT DOCUMENTS

| | | | |
|---|---|---|---|
| 3,757,127 | 9/1973 | Dhaka | 250/227 |
| 4,113,354 | 9/1978 | Yamasita et al. | 128/4 |
| 4,594,613 | 6/1986 | Shinbori et al. | 358/213.11 |
| 4,682,219 | 6/1987 | Arakawa | 358/98 |
| 4,692,608 | 9/1987 | Cooper et al. | 250/216 |
| 4,745,470 | 5/1988 | Yabe et al. | 358/98 |
| 4,773,396 | 9/1988 | Okasaki | 358/98 |
| 5,021,888 | 6/1991 | Kondou et al. | 358/213.11 |
| 5,040,069 | 8/1991 | Matsumoto et al. | 358/213.11 |

FOREIGN PATENT DOCUMENTS

| | | | |
|---|---|---|---|
| 0325525 | 1/1989 | European Pat. Off. | H01L 31/02 |
| 3715417 | 11/1987 | Germany | H04N 5/225 |
| 58-128762 | 8/1983 | Japan | H01L 27/14 |
| 59-161078 | 1/1985 | Japan | H01L 31/02 |
| 1-161775 | 6/1989 | Japan | H01L 31/02 |
| 2165092 | 4/1986 | United Kingdom | H01L 31/02 |

*Primary Examiner*—Michael T. Razavi
*Assistant Examiner*—Tuan V. Ho
*Attorney, Agent, or Firm*—Foley & Lardner

[57] ABSTRACT

An imaging apparatus for an electronic endoscope capable of realizing a compact size and improved optical characteristics simultaneously. In the apparatus, the imaging element is mounted on the rigid circuit substrate such that the substrate connection pads of the rigid circuit substrate and the element connection pads of the imaging element are electrically connected by a mutual compression bonding between the rigid circuit substrate and the imaging element, by a face-down bonding such that the imaging surface of the imaging element is facing toward the window of the rigid circuit substrate.

16 Claims, 4 Drawing Sheets

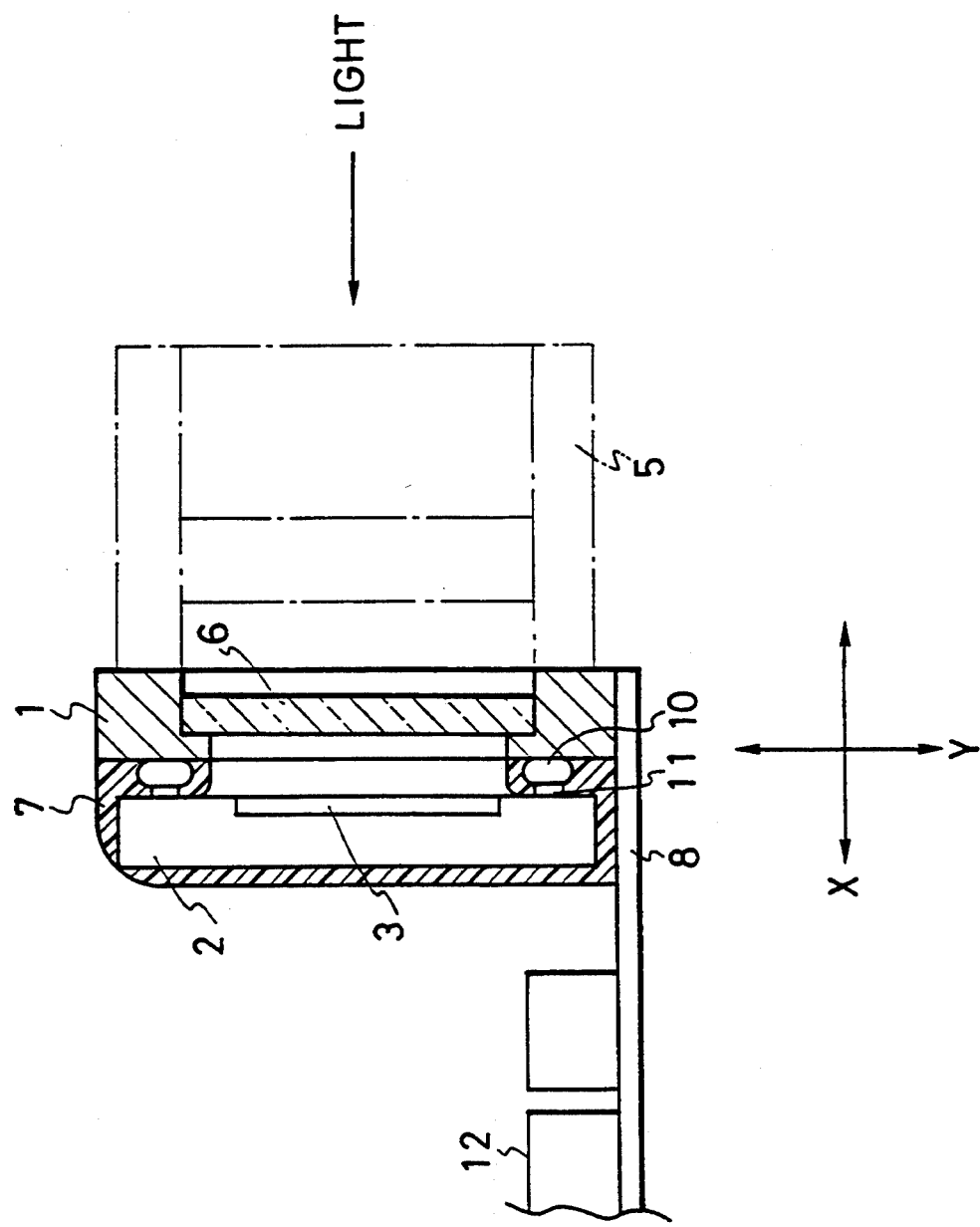

COMPACT IMAGING APPARATUS FOR ELECTRONIC ENDOSCOPE WITH IMPROVED OPTICAL CHARACTERISTICS

This application is a continuation of application Ser. No. 07/757,350, filed Sep. 10, 1991, now abandoned.

BACKGROUND OF THE INVENTION

1. Field of the Invention

The present invention relates to an imaging apparatus to be mounted on a scope end section of an electronic endoscope.

2. Description of the Background Art

Conventionally, an imaging apparatus for an electronic endoscope has a configuration shown in FIG. 1. In this conventional imaging apparatus of FIG. 1, a CCD (charge coupled device) 102 is fixed on one side of a chip carrier 101 made from a ceramic substrate, where pads 103 provided on the CCD 102 and pads 104 provided on the chip carrier 101 are connected by bonding wires 105. Then, a cover glass 106 containing an optical filter is attached on an imaging surface of the CCD 102 by means of an adhesive resin 111 placed therebetween, while the other side of the chip carrier 101 is attached to a flexible print substrate 107 such that they are electrically connected. In addition, the above described structure formed by the chip carrier 101, the CCD 102, the bonding wires 105, the cover glass 106, and the flexible print substrate 107 are covered by a mold resin 108, while the bonding wires 105 are protected by metallic frames 109 attached on the mold resin 108 over the locations of the bonding wires 105. Moreover, on a part of the flexible print substrate 107 not covered by the mold resin 108, chip components 110 are provided. With this configuration, the imaging apparatus is mounted on a scope end section of an electronic endoscope.

However, such a conventional imaging apparatus for an electronic endoscope has been associated with the following problems.

First, a conventional imaging apparatus with a configuration shown in FIG. 1 involves a number of piled up layers such as those for a height of the bonding wires 105, a distance between the bonding wires 105 and the metallic frames 109, a thickness of the chip carrier 101, a thickness of the metallic frames 109, a thickness of the flexible print substrate 107, and a thickness of the mold resin 108, so that a further thinning of a thickness of such an imaging apparatus has been practically impossible, and this in turn obstructed the further thinning of the scope end section of the electronic endoscope.

Secondly, the cover glass 106 is attached on the imaging surface of the CCD 102 by means of the adhesive resin 111 placed therebetween, such that micro-lenses (not shown) provided on the imaging surface of the CCD 102 are buried inside the adhesive resin 111. Here, because the index of refraction of the adhesive resin 111 is very close to that of the micro-lenses so that the light beam will hardly be refracted at a boundary between the adhesive resin 111 and the micro-lenses. As a consequence, an effect of improving a sensitivity of the CCD 102 due to the presence of the micro-lenses cannot be obtained.

Thirdly, the cover glass 106 cannot be made larger because of the possible interference between the cover glass 106 and the pads 103 of the CCD 102. As a result, it has been impossible to keep the reflections by the side surfaces of the cover glass 106 out of the imaging surface of the CCD 102.

Finally, in the imaging apparatus for an electronic endoscope, it is necessary to arrange the imaging surface of the CCD 102 to be perpendicular with respect to a light beam axis of an incident light beam. However, in the conventional imaging apparatus for an electronic endoscope, the cover glass 106 is attached on the imaging surface of the CCD 102 by means of the adhesive resin 111 placed therebetween as already mentioned above, so that it is difficult for the imaging surface of the CCD 102 to be arranged accurately in a desired direction because it is difficult to accurately control the thickness of the adhesive resin 111 during its hardening process.

SUMMARY OF THE INVENTION

It is therefore an object of the present invention to provide an imaging apparatus for an electronic endoscope capable of realizing a compact size and improved optical characteristics.

According to one aspect of the present invention there is provided an imaging apparatus for an electronic endoscope, comprising: a rigid circuit substrate having substrate connection pads; an imaging element having element connection pads, which is attached on the rigid circuit substrate such that the substrate connection pads of the rigid circuit substrate and the element connection pads of the imaging element are electrically connected by a mutual compression bonding between the rigid circuit substrate and the imaging element.

According to another aspect of the present invention there is provided an imaging apparatus for an electronic endoscope, comprising: a rigid circuit substrate having a window through which a light beam is entered; and an imaging element having an imaging surface, which is mounted on the rigid circuit substrate by a face-down bonding such that the imaging surface of the imaging element is facing toward the window of the rigid circuit substrate.

Other features and advantages of the present invention will become apparent from the following description taken in conjunction with the accompanying drawings.

BRIEF DESCRIPTION OF THE DRAWINGS

FIG. 4 is a cross sectional view of a third embodiment of an imaging apparatus for an electronic endoscope according to the present invention.

DETAILED DESCRIPTION OF THE PREFERRED EMBODIMENTS

Figure 1:
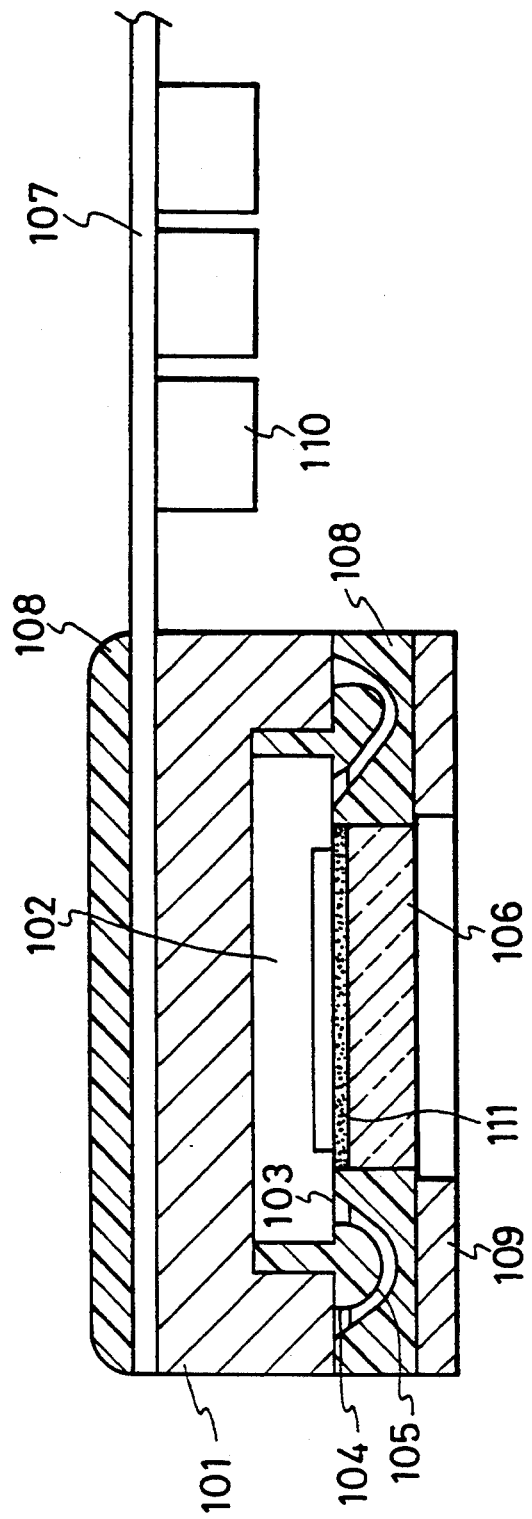
FIG. 1 is a cross sectional view of a conventional imaging apparatus for an electronic endoscope.
Figure 2A:
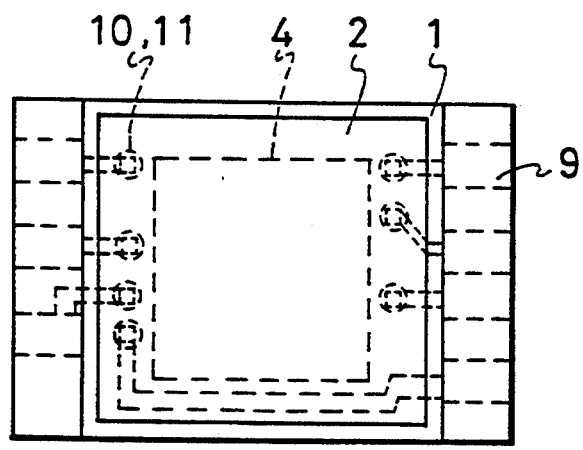
FIGS. 2(A) and 2(B) are a plan view and a cross sectional view of a first embodiment of an imaging apparatus for an electronic endoscope according to the present invention.
Figure 2B:
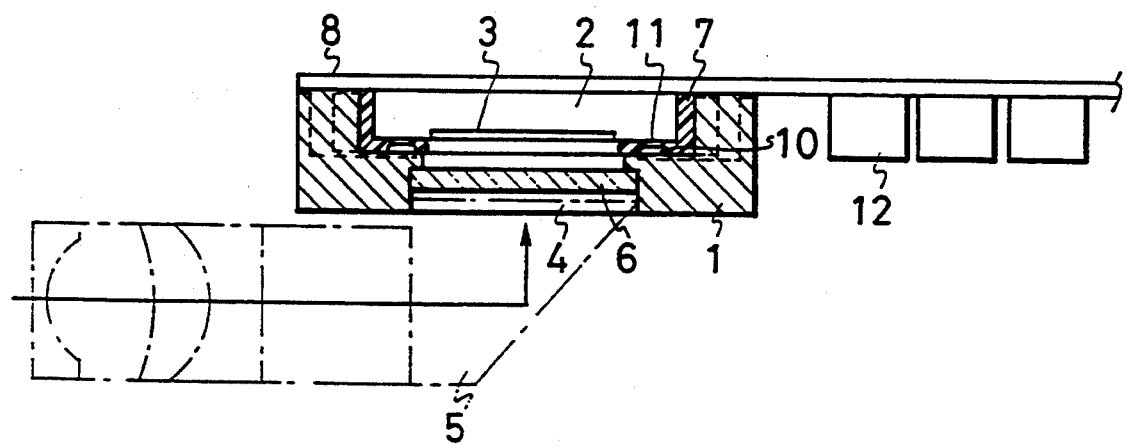
Figure 2B:
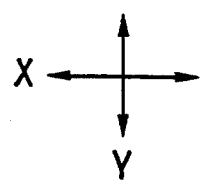

Referring now to FIGS. 2(A) and 2(B), a first embodiment of an imaging apparatus for an electronic endoscope according to the present invention will be described in detail.

This first embodiment is a case in which an imaging surface 3 of an imaging element such as a CCD (charge coupled device) 2 is provided in parallel to a scope axis direction X for a scope end section.

In this first embodiment, the imaging apparatus is formed by a ceramic substrate 1 having a central plate portion with a window 4 and side bank portions projecting upwards, where the CCD 2 is mounted on an upper side of the central plate portion of the ceramic substrate 1 by a face-down bonding such that the imaging surface 3 of the CCD 2 is facing toward the window 4 of the central plate portion of the ceramic substrate 1.

In the window 4 of the central plate portion of the ceramic substrate 1, there is provided a cover glass 6 such that a light beam entering from an object optical system 5 in a scope diameter direction Y toward the window 4 passes through this cover glass 6 so as to be transmitted to the imaging surface 3 of the CCD 2.

The CCD 2 is supported on the ceramic substrate 1 by means of a mold resin 7 inserted therebetween except for the location of the imaging surface 3, such that an air layer is formed between the cover glass 6 and the imaging surface 3 of the CCD 2.

Moreover, the ceramic substrate 1 has a multiple layers of wirings embedded and the embedded wirings are lead to electrodes 9 formed on the side bank portions of the ceramic substrate 1, such that the wirings in the ceramic substrate 1 can be electrically connected with a flexible print substrate 8 attached on the side bank portions of the ceramic substrate 1 through the electrodes 9. This flexible print substrate 8 also has a number of chip components 12 attached besides the ceramic substrate 1.

Furthermore, the central plate portion of the ceramic substrate 1 has pads 10 connected with the wirings inside the ceramic substrate 1 on the upper side of the central plate portion, while the CCD 2 has pads 11 in a vicinity of the imaging surface 3 such that when the CCD 2 is mounted on the central plate portion of the ceramic substrate 1 by the face-down bonding, the pads 10 of the ceramic substrate 1 and the pads 11 of the CCD 2 are electrically connected by a mutual compression bonding. Here, the pads 10 of the ceramic substrate 1 and the pads 11 of the CCD 2 may be formed with metallic or solder bumps provided such that the mutual compression bonding between the pads 10 of the ceramic substrate 1 and the pads 11 of the CCD 2 can be realized by a thermocompression bonding of the bumps.

Thus, according to this first embodiment, the electrical connection between the pads 10 of the ceramic substrate 1 and the pads 11 of the CCD 2 is obtained by mounting the CCD 2 on the central plate portion of the ceramic substrate 1 by the face-down bonding, so that no bonding wire for providing this electrical connection is necessary.

Consequently, this imaging apparatus of the first embodiment can be made thinner by a height of the bonding wires compared with a conventional imaging apparatus involving the bonding wires, which in turn contributes to the improvement of the maneuverability of the electronic endoscope in which the imaging apparatus of this first embodiment is used.

Moreover, in this first embodiment, there is no need to provide a covering of the bonding wires by the mold resin as well as a protection of the bonding wires by metallic frames, unlike a conventional imaging apparatus involving the bonding wires for which both of these are required. As a consequence, a configuration of the imaging apparatus can be made simpler than that of a conventional imaging apparatus as a number of components involved can be reduced.

Furthermore, because of the absence of the bonding wires, the cover glass 6 can be made sufficiently larger than the imaging surface 3 of the CCD 2, such that the reflections by the side surfaces of the cover glass 6 can be kept out of the imaging surface 3 of the CCD 2.

Also, the S/N ratio can be improved in this imaging apparatus as a result of the micro-lense effect obtained by the difference between the index of refraction of micro-lenses (not shown) provided on the imaging surface 3 of the CCD 2 and that of the air layer provided between the cover glass 6 and the imaging surface 3 of the CCD 2.

In addition, the application of the ultrasonic waves conventionally used in making the wire bonding of the pads becomes unnecessary, such that the wirings inside the ceramic substrate 1 can be designed freely without considering the effect due to the application of the ultrasonic waves.

Also, because of the use of the face-down bonding between the CCD 2 and the ceramic substrate 1 in which the imaging surface 3 of the CCD 2 can be arranged highly accurately, there is no adhesive layer involved between the CCD 2 and the ceramic substrate 1, such that the accuracy for arranging the imaging surface 3 of the CCD 2 to be perpendicular with respect to an incident light beam axis of the object optical system 5 can be improved, and therefore the optical characteristics of the imaging apparatus can be improved.

Figure 3A:
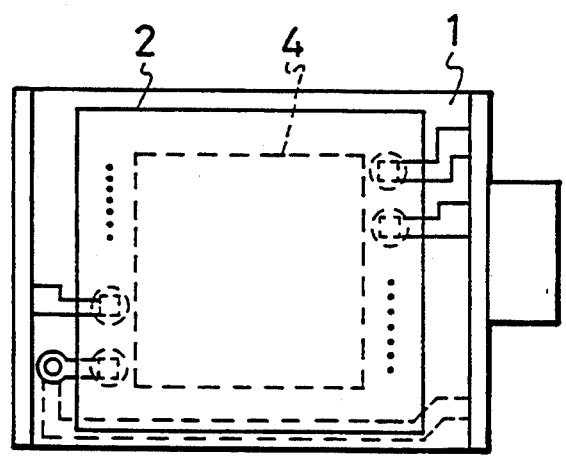
FIGS. 3(A) and 3(B) are a plan view and a cross sectional view of a second embodiment of an imaging apparatus for an electronic endoscope according to the present invention.
Figure 3B:
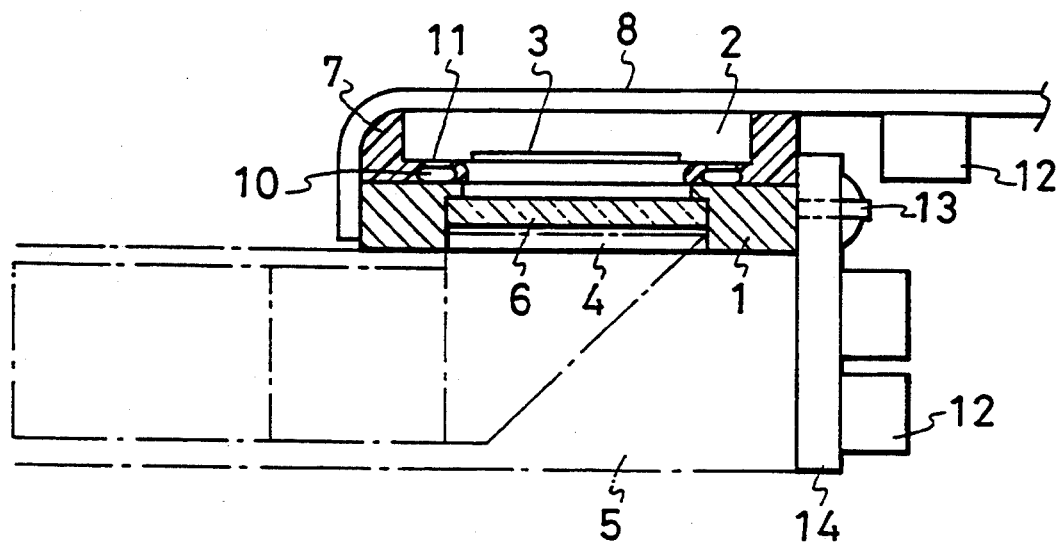
Figure 3B:
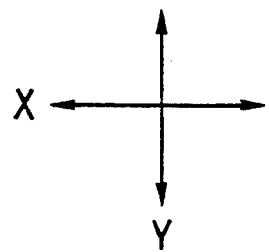

Referring now to FIGS. 3(A) and 3(B), a second embodiment of an imaging apparatus for an electronic endoscope according to the present invention will be described in detail. Here, those elements which are equivalent to corresponding elements in the first embodiment described above are given the same reference numerals in the figures.

This second embodiment is also a case in which an imaging surface 3 of a CCD 2 is provided in parallel to a scope axis direction X for a scope end section.

In this second embodiment, the imaging apparatus is formed by a ceramic substrate 1 having a central plate portion with a window 4, where the CCD 2 is mounted on an upper side of the central plate portion of the ceramic substrate 1 by a face-down bonding such that the imaging surface 3 of the CCD 2 is facing toward the window 4 of the central plate portion of the ceramic substrate 1.

In the window 4 of the central plate portion of the ceramic substrate 1, there is provided a cover glass 6 such that a light beam entering from an object optical system 5 in a scope diameter direction Y toward the window 4 passes through this cover glass 6 so as to be transmitted to the imaging surface 3 of the CCD 2.

The CCD 2 is supported on the ceramic substrate 1 by means of a mold resin 7 inserted therebetween except for the location of the imaging surface 3, such that an air layer is formed between the cover glass 6 and the imaging surface 3 of the CCD 2.

Moreover, the ceramic substrate 1 has a multiple layers of wirings embedded and the embedded wirings are lead to a junction board 13 attached on a side face of the ceramic substrate 1, where the junction board 13 is pierced into a print substrate 14 such that the wirings in the ceramic substrate 1 can be electrically connected with the print substrate 14 having a number of chip components 12 attached besides the ceramic substrate 1.

In addition, a flexible print substrate 8 which also has a number of chip components 12 attached is provided over the upper side of the CCD 2 and the side face of the ceramic substrate 1.

Furthermore, the central plate portion of the ceramic substrate 1 has pads 10 connected with the wirings inside the ceramic substrate 1 on the upper side of the central plate portion, while the CCD 2 has pads 11 in a vicinity of the imaging surface 3 such that when the CCD 2 is mounted on the central plate portion of the ceramic substrate 1 by the face-down bonding, the pads 10 of the ceramic substrate 1 and the pads 11 of the CCD 2 are electrically connected by a mutual compression bonding.

Thus, according to this second embodiment, the imaging apparatus can be further shortened in the scope axis direction X compared with the first embodiment described above, while maintaining the other advantages similar to those described above for the first embodiment.

Referring now to FIG. 4, a third embodiment of an imaging apparatus for an electronic endoscope according to the present invention will be described in detail. Here, those elements which are equivalent to corresponding elements in the first embodiment described above are given the same reference numerals in the figures.

This third embodiment is a case in which an imaging surface 3 of a CCD 2 is provided along a scope diameter direction Y perpendicular to a scope axis direction X for a scope end section.

In this third embodiment, the imaging apparatus is formed by a ceramic substrate 1 having a central plate portion with a window 4, where the CCD 2 is mounted on an upper side of the central plate portion of the ceramic substrate 1 by a face-down bonding such that the imaging surface 3 of the CCD 2 is facing toward the window 4 of the central plate portion of the ceramic substrate 1.

In the window 4 of the central plate portion of the ceramic substrate 1, there is provided a cover glass 6 such that a light beam entering from an object optical system 5 in the scope axis direction X toward the window 4 passes through this cover glass 6 so as to be transmitted to the imaging surface 3 of the CCD 2.

The CCD 2 is supported on the ceramic substrate 1 by means of a mold resin 7 inserted therebetween except for the location of the imaging surface 3, such that an air layer is formed between the cover glass 6 and the imaging surface 3 of the CCD 2.

Moreover, the ceramic substrate 1 has a multiple layers of wirings embedded and the embedded wirings are lead to a side face of the ceramic substrate 1, such that the wirings in the ceramic substrate 1 can be electrically connected with a flexible print substrate 8 attached on the side face of the ceramic substrate 1. This flexible print substrate 8 also has a number of chip components 12 attached besides the ceramic substrate 1.

Furthermore, the central plate portion of the ceramic substrate 1 has pads 10 connected with the wirings inside the ceramic substrate 1 on the upper side of the central plate portion, while the CCD 2 has pads 11 in a vicinity of the imaging surface 3 such that when the CCD 2 is mounted on the central plate portion of the ceramic substrate 1 by the face-down bonding, the pads 10 of the ceramic substrate 1 and the pads 11 of the CCD 2 are electrically connected by a mutual compression bonding.

Thus, according to this third embodiment, in addition to the other advantages similar to those described above for the first embodiment, the imaging apparatus can be further shortened in the scope axis direction X compared with the first embodiment described above, so that it becomes possible to shorten a hard portion in a scope end section of an electronic endoscope in which the imaging apparatus of this third embodiment is used, which in turn contributes to the improved maneuverability of the electronic endoscope.

It is to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An imaging apparatus for an electronic endoscope, comprising:
   an optical system for deflecting a light beam entering into a scope end section of the electronic endoscope by 90 degrees;
   a rigid circuit substrate, having substrate connection pads, electrodes, and a window through which the light beam deflected by the optical system passes, the window being defined by a smaller opening on a first side from which the light beam goes out of the window and a larger opening on a second side into which the light beam is entered from the optical system;
   an imaging element having an imaging surface for receiving the light beam deflected by the optical system through the window of the rigid circuit substrate, and element connection pads, both of which are located on one side of the imaging element, the imaging element being attached on the rigid circuit substrate such that the substrate connection pads of the rigid circuit substrate and the element connection pads of the imaging element are electrically connected by a mutual compression bonding between the rigid circuit substrate and the imaging element, the imaging element being arranged such that the imaging surface of the imaging element is located over the first side and facing towards the first side of the window and positioned in parallel to a direction of a scope axis of the scope and section of the electronic endoscope;
   a cover glass fitted within the window of the rigid circuit substrate for covering the second side of the window; and
   an insulative flexible print substrate connected with the electrodes of the rigid circuit substrate, which covers a side of the imaging element opposite to said one side,
   wherein the window of the rigid circuit substrate spatially separates the cover glass from the imaging surface of the imaging element by placing the cover glass between the first side and the second side so as to define an air layer between the cover glass and the imaging surface.

2. The imaging apparatus of claim 1, wherein the rigid circuit substrate has connection wirings embedded within the rigid circuit substrate, where the connection wirings are connected with the substrate connection pads.

3. The imaging apparatus of claim 1, wherein the rigid circuit substrate is made of a ceramic substrate.

4. The imaging apparatus of claim 1, wherein the imaging surface of the imaging element has micro-lenses provided thereon, for causing a micro-lens effect for converting light due to a difference between an index of refraction of the micro-lenses and an index of refraction of the air layer defined between the cover glass and the imaging surface.

5. The imaging apparatus of claim 1, wherein the rigid circuit substrate has a central plate portion on which the window is formed, and side bank portions projecting upwards from the central plate portion for defining a position for mounting the imaging element on the central plate portion over the upper side of the window.

6. An imaging apparatus for an electronic endoscope, comprising:

an optical system for deflecting a light beam entering into a scope end section of the electronic endoscope by 90 degrees;

a rigid circuit substrate, having substrate connection pads, electrodes, and a window through which the light beam deflected by the optical system passes, the window being defined by a smaller opening on a first side from which the light beam goes out of the window and a larger opening on a second side into which the light beam is entered from the optical system;

an imaging element having an imaging surface for receiving the light beam deflected by the optical system through the window of the rigid circuit substrate, and element connection pads, both of which are located on one side of the imaging element, the imaging element being attached on the rigid circuit substrate such that the substrate connection pads of the rigid circuit substrate and the element connection pads of the imaging element are electrically connected by a mutual compression bonding between the rigid circuit substrate and the imaging element the imaging element being arranged such that the imaging surface of the imaging element is located over the first side and facing toward the first side of the window and positioned in parallel to a direction of a scope axis of the scope end section of the electronic endoscope;

a cover glass fitted within the window of the rigid circuit substrate for covering the second side of the window; and an insulative flexible print substrate connected with the electrodes of the rigid circuit substrate, which covers a side of the imaging element opposite to said one side, wherein the window of the rigid circuit substrate specially separates the cover glass from the imaging surface of the imaging element by placing the cover glass between the first side and the second side so as to define an air layer between the cover glass and the imaging surface, wherein the rigid circuit substrate bas a window through which the light beam deflected by the optical system passes, and the imaging surface of the imaging element faces toward the window of the rigid circuit substrate;

a cover glass provided in the window Of the rigid circuit substrate, where the cover glass is separated from the imaging surface of the imaging element by an air layer, wherein the cover glass has a size sufficiently larger than that of the imaging surface of the imaging element such that end surface reflections of the light beam entering through the window of the rigid circuit substrate due to the cover glass can be kept out of the imaging surface of the imaging element.

7. An imaging apparatus for an electronic endoscope, comprising:

an optical system for deflecting a light beam entering into a scope end section of the electronic endoscope by 90 degrees;

a rigid substrate having electrodes and a window through which the light beam passes, the window being defined by a smaller opening on a first side from which the light beam goes out of the window and a larger opening on a second side into which the light beam enters from the optical system;

an imaging element having an imaging surface, located on one side of the imaging element, for receiving the light beam deflected by the optical system through the window of the rigid circuit substrate, the imaging element being mounted on the rigid circuit substrate by a face-down bonding such that the imaging surface of the imaging element is facing toward the first side and located over the first side of the window of the rigid circuit substrate, and the imaging element is arranged such that the imaging surface of the imaging element is positioned in parallel to a direction of a scope axis of the scope end section of the electronic endoscope;

a cover glass fitted within the window of the rigid circuit substrate for covering the second side of the window; and an insulative flexible print substrate connected with the electrodes of the rigid circuit substrate, which covers a side of the imaging element opposite to said one side, wherein the window of the rigid circuit substrate spatially separates the cover glass from the imaging surface of the imaging element by placing the cover glass between the first side and the second side so as to define an air layer between the cover glass and the imaging surface.

8. The imaging apparatus of claim 7, wherein the rigid circuit substrate has connection wirings embedded within the rigid circuit substrate, where the connection wirings are connected with the substrate connection pads.

9. The imaging apparatus of claim 7, wherein the rigid circuit substrate is made of a ceramic substrate.

10. The imaging apparatus of claim 7, wherein the imaging surface of the imaging element has micro-lenses provided thereon, for causing a micro-lens effect for converting light due to a difference between an index of refraction of the micro-lenses and an index of refraction of the air layer defined between the cover glass and the imaging surface.

11. The imaging apparatus of claim 7, wherein the rigid circuit substrate has a central plate portion on which the window is formed, and side bank portions projecting upwards from the central plate portion for defining a position for mounting the imaging element on the central plate portion over the upper side of the window.

12. An imaging apparatus for an electronic endoscope comprising:

an optical system for deflecting a light beam entering into a scope end section of the electronic endoscope by 90 degrees;

a rigid circuit substrate having electrodes and a window through which the light beam passes, the window being defined by a smaller opening on a first side and a larger opening on a second side into which the light beam is entered from the optical system;

an imaging element having an imaging surface, located on one side of the imaging element, for receiving the light beam deflected by the optical system through the window of the rigid circuit substrate, the imaging element being mounted on the rigid circuit substrate by a face-down bonding such that the imaging surface of the imaging element is facing toward the first side and facing towards the first side of the window of the rigid circuit substrate, and the imaging element is arranged such that the imaging surface of the imaging element is positioned in parallel to a direction of a scope axis of the scope end section of the electronic endoscope;

a cover glass fitted within the window of the rigid circuit substrate for covering the second side of the window;

an insulative flexible print substrate connected with the electrodes of the rigid circuit substrate which covers a side of the imaging element opposite to said one side, wherein the window of the rigid circuit substrate spatially separates the cover glass from the imaging surface of the imaging element by placing the cover glass between the first side and the second side so as to define an air layer between the cover glass and the imaging surface, wherein the rigid circuit substrate has substrate connection pads on one side facing toward the imaging element, and the imaging element has element connection pads on said one side of the imaging element which is facing toward the rigid circuit substrate, such that the substrate connection pads of the rigid circuit substrate and the element connection pads of the imaging element are electrically connected by a mutual compression bonding between the rigid circuit substrate and the imaging element; and a cover glass provided in the window of the rigid circuit substrate, where the cover glass is separated from the imaging surface of the imaging element by an air layer, wherein the cover glass has a size sufficiently larger than that of the imaging surface of the imaging element such that end surface reflections of the light beam entering through the window of the rigid circuit substrate due to the cover glass can be kept out of the imaging surface of the imaging element.

13. An imaging apparatus for an electronic endoscope, comprising:

a rigid circuit substrate, having substrate connection pads, electrodes, and a window through which a light beam passes, the window being defined by a smaller opening on a first side from which the light beam goes out of the window and a larger opening on a second side into which the light beam enters;

an imaging element, having element connection pads and an imaging surface facing towards the first side and located over the first side of the window of the rigid circuit substrate, which is secured to the rigid circuit substrate such that the substrate connection pads of the rigid circuit substrate and the element connection pads of the imaging element are electrically connected by a mutual compression bonding between the rigid circuit substrate and the imaging element;

a cover glass fitted within the window of the rigid circuit substrate for covering the second side of the window; and an insulative flexible print substrate connected with the electrodes of the rigid circuit substrate, wherein the window of the rigid circuit substrate spatially separates the cover glass from the imaging surface of the imaging element by placing the cover glass between the first side and the second side so as to define an air layer between the cover glass and the imaging surface.

14. The imaging apparatus of claim 13, wherein the cover glass has a size sufficiently larger than that of the imaging surface of the imaging element such that end surface reflections of the light beam entering through the window of the rigid circuit substrate due to the cover glass can be kept out of the imaging surface of the imaging element.

15. An imaging apparatus for an electronic endoscope, comprising:

a rigid circuit substrate having electrodes and a window through which a light beam passes, the window being defined by a smaller opening on a first side from which the light beam goes out of the window and a larger opening on a second side into which the light beam is entered;

an imaging element having an imaging surface, said imaging element mounted on the rigid circuit substrate by a face-down bonding such that the imaging surface of the imaging element is facing toward the first side and located over the first side of the window of the rigid circuit substrate;

a cover glass fitted within the window of the rigid circuit substrate for covering the second side of the window; and an insulative flexible print substrate connected with the electrodes of the rigid circuit substrate, wherein the window of the rigid circuit substrate spatially separates the cover glass from the imaging surface of the imaging element by placing the cover glass between the first so as to define an air layer between the cover glass and the imaging surface.

16. The imaging apparatus of claim 15, wherein the cover glass has a size sufficiently larger than that of the imaging surface of the imaging element such that end surface reflections of the light beam entering through the window of the rigid circuit substrate due to the cover glass can be kept out of the imaging surface of the imaging element.

* * * * *